(12) United States Patent
Rokita et al.

(10) Patent No.: US 7,390,832 B2
(45) Date of Patent: Jun. 24, 2008

(54) DINUCLEAR COPPER-BASED COMPOUND AND LIGAND FOR NUCLEIC ACID SCISSION AND ANTICANCER TREATMENT

(75) Inventors: Steven E. Rokita, Sliver Spring, MD (US); Kenneth D. Karlin, Owings Mills, MD (US); Lei Li, Baltimore, MD (US); Narasimha N. Murthy, Madras (IN)

(73) Assignees: The University of Maryland, College Park, MD (US); The Johns Hopkins University, Baltimore, MD (US)

( * ) Notice: Subject to any disclaimer, the term of this patent is extended or adjusted under 35 U.S.C. 154(b) by 434 days.

(21) Appl. No.: 10/492,197

(22) PCT Filed: Nov. 12, 2002

(86) PCT No.: PCT/US02/36082

§ 371 (c)(1),
(2), (4) Date: Dec. 2, 2004

(87) PCT Pub. No.: WO03/052058

PCT Pub. Date: Jun. 26, 2003

(65) Prior Publication Data

US 2005/0148662 A1 Jul. 7, 2005

Related U.S. Application Data

(60) Provisional application No. 60/331,198, filed on Nov. 9, 2001.

(51) Int. Cl.
*A01N 55/02* (2006.01)
*A61K 31/30* (2006.01)
*A61K 31/555* (2006.01)
*C07F 1/00* (2006.01)
*C07F 15/00* (2006.01)
*C07H 21/02* (2006.01)
*C07H 21/04* (2006.01)

(52) U.S. Cl. .................. 514/499; 556/113; 546/2; 514/184; 536/23.1

(58) Field of Classification Search .................. None
See application file for complete search history.

(56) References Cited

U.S. PATENT DOCUMENTS 6,143,879 A  11/2000  Que, Jr. et al.
6,765,104 B1 *  7/2004  Brechbiel et al. .......... 556/110

OTHER PUBLICATIONS

Sorrell et. al.; Inorganica Chimica Acta (1989), 166(1), 71-77.*
Sorrell et. al.; J.Am.Chem.Soc. 1985, 107, 4199-4206.*
Humphreys et al., Efficient and Specific Strand Scission of DNA by a Dinuclear Cooper Complex: Comparative Reactivity of Complexes with Linked Tris(2-pyridylmethly)amine Moieties, Journal of the American Chemical Society, May 29, 2002, vol. 124, pp. 6009-6019.

* cited by examiner

*Primary Examiner*—James O. Wilson
*Assistant Examiner*—Jeffrey H Murray
(74) *Attorney, Agent, or Firm*—Arent Fox LLP

(57) ABSTRACT

The present invention is related to a novel method for oxidizing or splitting nucleic acids at specific points on a complementary nucleic acid segment using a dinuclear copper-based compound of Formula I. Additionally, the present invention is related to a novel treatment of cancer, tumors, and cancer cells using a dinuclear copper-based compound of formula I or a naked ligand of Formula II.

26 Claims, 4 Drawing Sheets

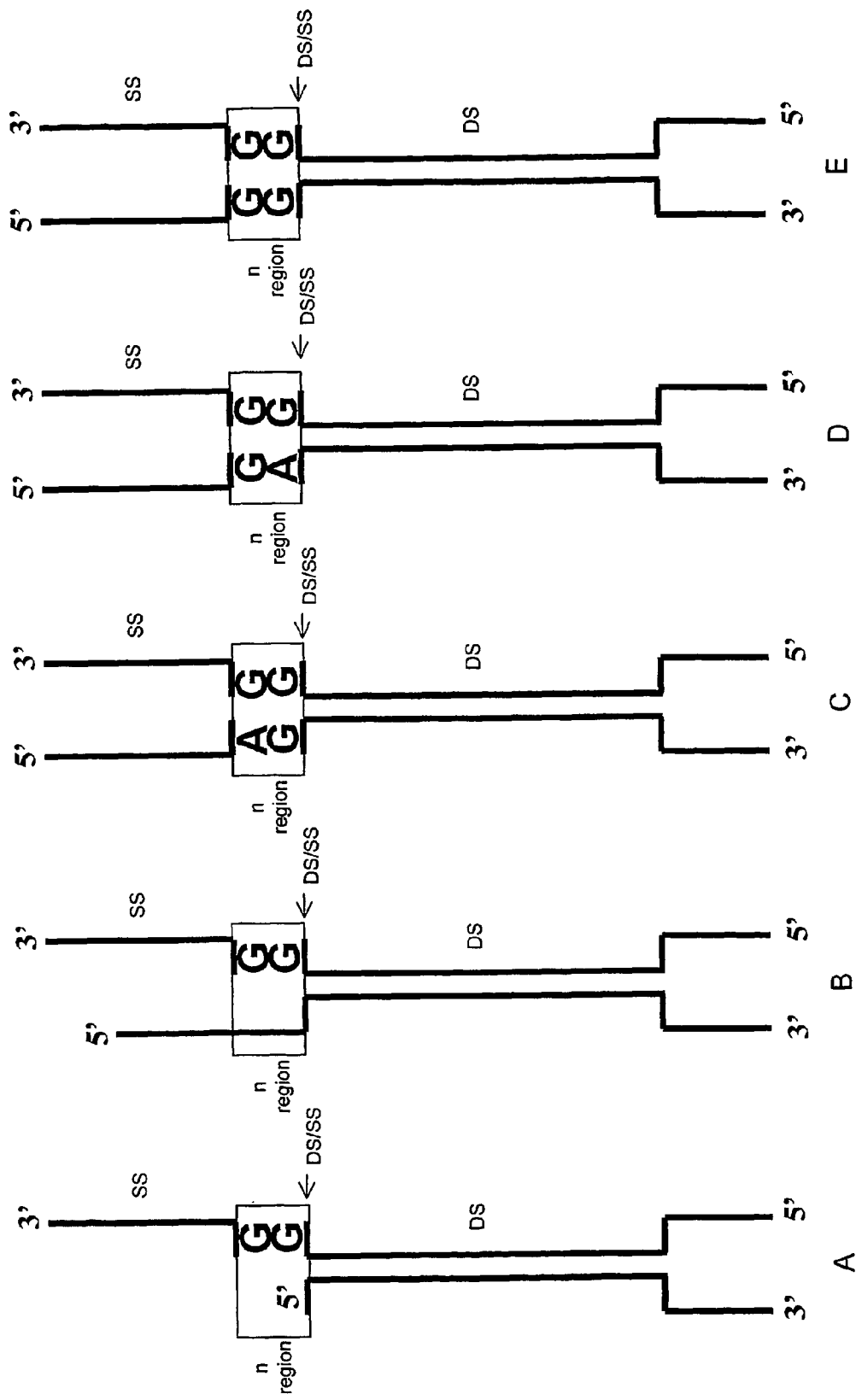

US 7,390,832 B2

DINUCLEAR COPPER-BASED COMPOUND AND LIGAND FOR NUCLEIC ACID SCISSION AND ANTICANCER TREATMENT

This is a §371 of International Patent Application No. PCT/USO2/36082 filed on Nov. 12, 2002, which is based on U.S. Provisional Application Ser. No. 60/331,198 filed on Nov. 9, 2001. The disclosure of the prior applications are hereby incorporated by reference herein in its entirety.

The United States Government has rights in this invention pursuant to Grants No GM28962 and GM47351 awarded by the National Institutes of Health (NIH).

FIELD OF INVENTION

The present invention is related to a novel method for oxidizing and splitting (if exposed to piperidine) nucleic acids at specific points on a nucleic acid segment using a dinuclear copper-based compound. Additionally, the present invention is related to a novel treatment of cancer, tumors, and cancer cells using a dinuclear copper-based compound or the naked ligand.

BACKGROUND OF INVENTION

A number of transition metal complexes have been found to be able to differentiate between double- vs. single-stranded DNA or B vs. Z helical forms of DNA through noncovalent recognition. This selectivity is primarily due to the binding of the transition metal complex in either the major or minor groove of duplex structures or in association with the nucleobases in unpaired strands. The electron-rich character of the nucleobases often makes them strong ligands for metals and efficient targets of oxidation. Guanine has been shown to have the highest affinity for coordination to transition metal ions and it is also the most easily oxidized, followed by adenine, cytosine and thymine (in order of ease of oxidation). Although base oxidation can be highly specific and directed to one site, strand scission has been shown to result from base oxidation only after treatment with subsequent heat and alkaline conditions.

Some complexes that exhibit direct strand cleavage in conjunction with sequence specificity are bleomycin.Fe(II) and the metallointercalator, $[Rh(phen)_2phi]^{3+}$. Although there is both a structural and a sequence requirement in each of these cases, the recognition criteria are not sufficiently unique to limit the number of target sites in DNA. Scission may be targeted specifically to one site by incorporating known DNA recognition elements into the ligand suprastructure of a well-characterized nucleolytic agent such as EDTA.Fe(II), which, when underivatized, promotes oxidative cleavage of DNA in a random fashion without nucleotide sequence selectivity. While this approach localizes cleavage to a site where the recognition element binds to DNA, the reaction is rarely constrained to a single nucleotide. Strand cleavage frequently extends over more than 5 bases. A longstanding goal of considerable interest has been to construct transition metal complexes that can mediate base oxidation and strand scission targeted to a single base with a significantly high level of recognition such that cleavage occurs at a limited number of sites along a target polynucleotide.

Most investigations focusing on oxidative strand scission of DNA by transition metals have typically relied on mononuclear complexes. Among these complexes, bis(1,10-phenanthroline)copper, $[Cu(OP)_2]^{2+}$, has been studied extensively due to its high nucleolytic efficiency. The cleavage pattern induced by $[Cu(OP)_2]^{2+}$ is predominantly sequence-neutral, although some variability in intensity due to local perturbations of DNA structure affects its efficiency. Also a slight, but distinct, preference for cleavage at 5'-AT-3' and 5'-GT-3' sites has been observed. Otherwise, $[Cu(OP)_2]^{2+}$ like EDTA.Fe(II) may be conjugated to binding elements such as proteins and complementary sequences of RNA or DNA that possess affinity for specific sites on DNA. Still, multiple sites adjacent to the locus of recognition are typically oxidized by these complexes even when tethered to a DNA recognition element.

SUMMARY OF INVENTION

The present invention is based on the discovery that certain dinuclear copper-based compounds possess the ability to recognize and promote oxidation and allow for scission of a nucleic acid at specific positions. Additionally, it has been discovered that the dinuclear copper-based compounds and the naked ligand possess the ability to treat cancer.

Thus, the invention is directed towards a method of treating cancer in a patient in need thereof, comprising administering to a patient a cancer-treating effective amount of a compound of formula I,

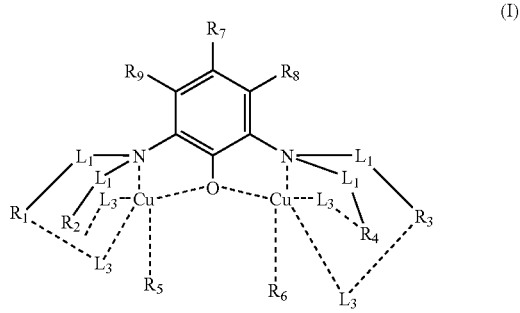

(I)

wherein:

$R_1$-$R_4$ are each independently (a) a 5 to 6 membered heterocycle containing 1-3 nitrogen atoms and optionally one oxygen atom, with the remainder of the atoms being carbon atoms, wherein the heterocycle is linked to a respective linkage $L_3$ through a nitrogen atom of the heterocycle, and wherein the heterocycle is linked to a respective linkage $L_1$ through any of the nitrogen or carbon atoms of the heterocycle other than the nitrogen atom that links to linkage $L_3$; and wherein the 5 to 6 membered heterocycle is unsubstituted or substituted with 1-3 substituents selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide or (b) an aromatic or cycloalkyl $C_9$-$C_{13}$ bicycle containing 1-3 nitrogen atoms and optionally one oxygen atom, with the remainder of the atoms being carbon atoms, wherein the bicycle is linked to a respective linkage $L_3$ through a nitrogen atom of the bicycle, and wherein the bicycle is linked to a respective linkage $L_1$ through any of the nitrogen or carbon atoms of the bicycle other than the nitrogen atom that links to linkage $L_3$, and wherein said aromatic or cycloalkyl $C_9$-$C_{13}$ bicycle is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide;

$R_5$-$R_6$ are each independently an anion or uncharged species;

$R_7$ is a hydrogen, halogen, hydroxy, or a $C_1$-$C_6$ alkyl group;

$R_8$-$R_9$ are each independently a hydrogen, hydroxy, a $C_1$-$C_3$ alkyl group, or a halogen;

each $L_1$ is independently a $C_1$-$C_6$ alkyl or ether linkage; and each $L_3$ is a direct bond.

The invention is further directed towards a method of treating a cancer tumor, said method comprising administering to the cancer tumor a cancer tumor-treating effective amount of a compound of formula I.

The invention is additionally directed towards a method of treating cancer cells, said method comprising administering to the cancer cells a cancer cell-treating effective amount of a compound of formula I.

The invention is directed towards a compound of formula I.

The invention is further directed towards a use of a compound of formula I to treat cancer.

The invention is further directed towards the use of a compound of formula I to prepare a medicament suitable for treating cancer.

The invention is further directed towards a method of oxidizing a nucleic acid segment at a specific position thereon, wherein said method comprises (A) providing a nucleic acid segment having at least one double-strand segment and at least one single-strand segment, and including an n region, wherein said n region is located either at or a number of base pairs from a double-strand/single-strand (ds/ss) junction on the single-strand segment of the nucleic acid, and the n region comprises two contiguous guanine residues located on a same strand of the nucleic acid segment; (B) contacting the nucleic acid segment with a compound of formula I for a time sufficient to oxidize at least one of the guanine residues of the n region; and oxidation will damage the guanine(s), thereby rendering the gene non-functional.

The invention is further directed towards a method of splitting a nucleic acid segment at a specific position thereon, wherein said method comprises (A) providing a nucleic acid segment having at least one double-strand segment and at least one single-strand segment, and including an n region, wherein said n region is located either at or a number of base pairs from a double-strand/single-strand (ds/ss) junction on the single-strand segment of the nucleic acid, and the n region comprises two contiguous guanine residues located on a same strand of the nucleic acid segment; (B) contacting the nucleic acid segment with a compound of formula I for a time sufficient to oxidize at least one of the guanine residues of the n region; and (C) thereafter contacting the nucleic acid segment with an amount of piperidine for a time sufficient to split the nucleic acid segment at the at least one oxidized guanine.

The invention is further directed towards a method of treating cancer in a patient in need thereof, said method comprising administering to a patient a cancer-treating effective amount of a compound of formula II,

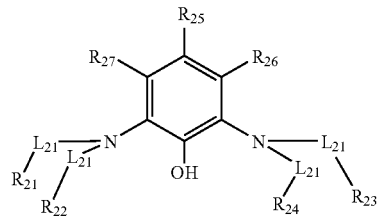

(II)

wherein:

$R_{21}$-$R_{24}$ are each independently (a) a 5 to 6 membered heterocycle containing 1-3 nitrogen atoms and optionally one oxygen atom, with the remainder of the atoms being carbon atoms, wherein the heterocycle is linked to a respective linker $L_{21}$ through a carbon or nitrogen atom of the heterocycle; and wherein the 5 to 6 membered heterocycle is unsubstituted or substituted with halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, phenyloxycarbonylamino, naphthyloxycarbonylamino, semicarbazido, heteroaryl, 4-acetoxyphenyloxy, phenyl or acetamide or (b) an aromatic or cycloalkyl $C_9$-$C_{13}$ bicycle containing 1-3 nitrogen atoms and optionally one oxygen atom, with the remainder of the atoms being carbon atoms, wherein the bicycle is linked to a respective linkage $L_{21}$ through a nitrogen atom of the bicycle, and wherein said aromatic or cycloalkyl $C_9$-$C_{13}$ bicycle is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide;

$R_{25}$ is a hydrogen, halogen, hydroxy, or a $C_1$-$C_6$ alkyl group;

$R_{26}$-$R_{27}$ are each independently a hydrogen, hydroxy, a $C_1$-$C_3$ alkyl group, or a halogen; and each $L_{21}$ is independently a $C_1$-$C_6$ alkyl or ether linkage.

The invention is further directed towards a method of treating a cancer tumor, said method comprising administering to the cancer tumor a cancer tumor-treating effective amount of a compound of formula II.

The invention is further directed towards a method of treating cancer cells, said method comprising administering to the cancer cells a cancer cell-treating effective amount of a compound of formula II.

The invention is further directed towards a use of a compound of formula II to treat cancer.

The invention is further directed towards the use of a compound of formula II to prepare a medicament suitable for treating cancer.

The invention is also directed towards a pharmaceutical composition containing a pharmaceutically effective amount of at least one compound of formula I.

The invention is also directed towards a pharmaceutical composition containing a pharmaceutically effective amount of at least one compound of formula II.

BRIEF DESCRIPTION OF THE DRAWINGS

FIG. 2a illustrates a sample nucleic acid segment containing a double-strand segment, a single-strand segment, and an n region at the ds/ss junction. FIG. 2a also illustrates the situation in which neither of the two contiguous guanine residues possess a corresponding residue.

FIG. 2b illustrates a sample nucleic acid segment containing a double-strand segment, a single-strand segment, and an n region at the ds/ss junction. FIG. 2b also illustrates the situation in which both of the two contiguous guanine residues possess a corresponding residue, wherein the corresponding residues are either adenine, thymine, or uracil.

FIG. 2c illustrates a sample nucleic acid segment containing a double-strand segment, a single-strand segment, and an n region at the ds/ss junction. FIG. 2c also illustrates the situation in which one of the two contiguous guanine residues has a corresponding residue that is adenine, thymine, or uracil and the other contiguous guanine residue has a corresponding residue that is guanine.

FIG. 2d illustrates a sample nucleic acid segment containing a double-strand segment, a single-strand segment, and an n region at the ds/ss junction. FIG. 2d also illustrates the situation in which one of the two contiguous guanine residues has a corresponding residue that is adenine, thymine, or uracil and the other contiguous guanine residue has a corresponding residue that is guanine. FIG. 2d differs from FIG. 2c in that the contiguous guanine residue that has a corresponding guanine residue is reversed.

FIG. 2e illustrates a sample nucleic acid segment containing a double-strand segment, a single-strand segment, and an n region at the ds/ss junction. FIG. 2e also illustrates the situation in which both of the two contiguous guanine residues possess a corresponding residue which is guanine.

FIG. 3a illustrates a sample nucleic acid segment containing a single-strand segment, a double-strand segment, a ds/ss junction, and an n region at the ds/ss junction.

FIG. 3b illustrates a sample nucleic acid segment containing a single-strand segment, a double-strand segment, a ds/ss junction, and an n region a number of bases away from the ds/ss junction, as compared to FIG. 3a.

FIG. 3c illustrates a sample nucleic acid segment containing a single-strand segment, a double-strand segment, a ds/ss junction, and an n region a larger number of bases away from the ds/ss junction, as compared to FIG. 3b.

FIG. 3d illustrates a sample nucleic acid segment containing a single-strand segment, a double-strand segment, a ds/ss junction, and an n region an even larger number of bases away from the ds/ss junction, as compared to FIG. 3c.

DETAILED DESCRIPTION OF THE PREFERRED EMBODIMENTS

Figure 1A:
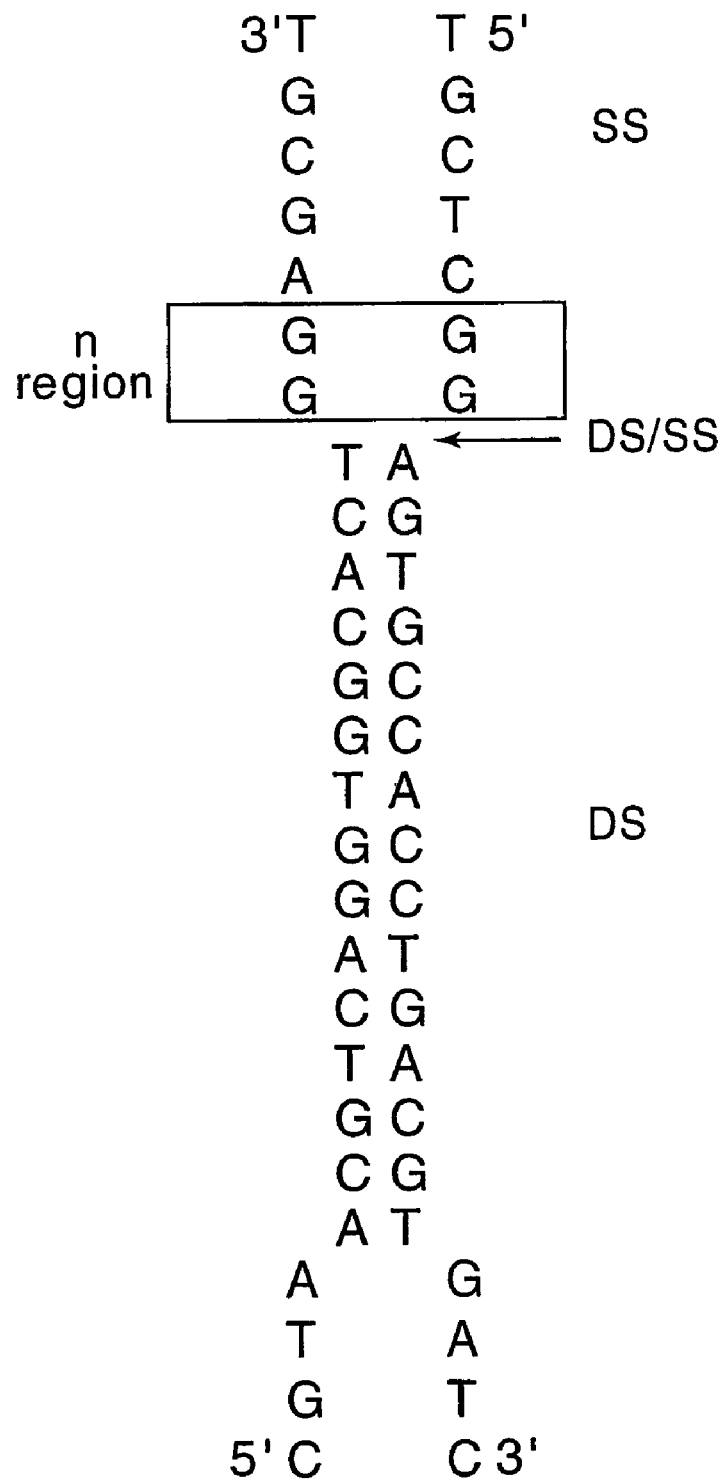
FIG. 1a illustrates a sample nucleic acid segment containing a double-strand segment, a single-strand segment, a ds/ss junction, and an n region.
Figure 1B:
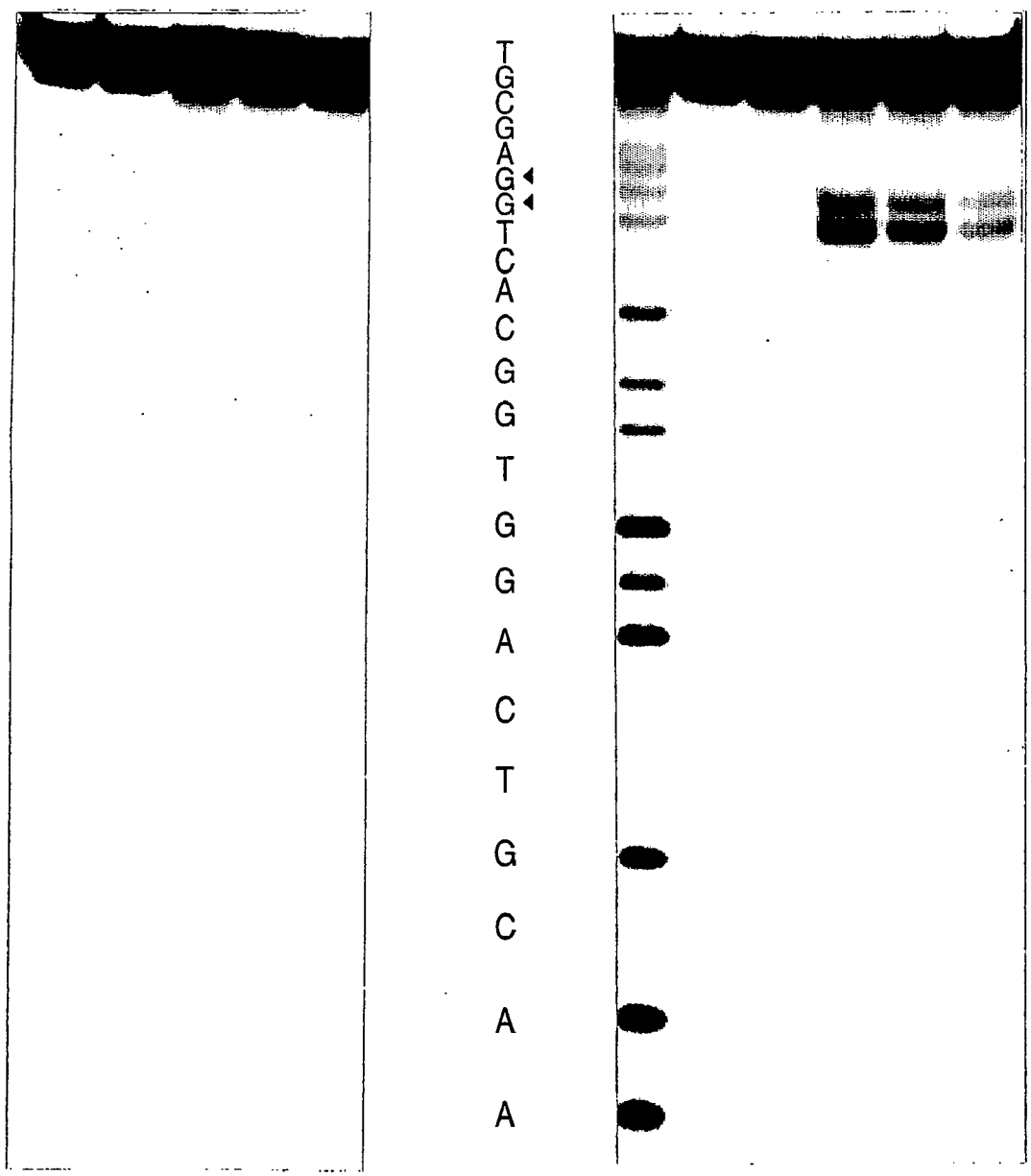
FIG. 1b illustrates a gel electrophoresis of the one of the strands of the sample nucleic acid segment when interacted with a compound of the invention.

The present invention is directed to novel uses of dinuclear copper-based compounds and the naked ligand thereof.

The term "nucleic acid segment" includes double-stranded and single-stranded DNA and RNA.

The term "segment" is intended to define either (1) a contiguous nucleic acid sequence on a nucleic acid strand or (2) an entire nucleic acid strand, whether it be a double-stranded or single-stranded nucleic acid strand.

The term "corresponding nucleic acid segment" is intended to refer to a nucleic acid segment on an opposing strand of the nucleic acid segment (i.e., the 5' strand would contain the corresponding nucleic acid segment for the 3' strand and vice versa).

The term "corresponding residue" is intended to refer to the location of a residue that is directly opposite from the residue on the corresponding nucleic acid segment, whether the corresponding residue is complementary or non-complementary.

The term "base pairs" is intended to refer to two nucleic acid residues directly opposed to each other (i.e., on the 3' and 5' strands) in a nucleic acid, regardless of complementarity (i.e., whether it be a purine-purine pair, a pyrimidine-pyrimidine pair, or a pyrimidine-purine pair). In reference to a "single-strand segment" which lacks a corresponding 3' or 5' strand, the term "base pair" can apply to a single pyrimidine or single purine without a corresponding nucleic acid residue.

The term "double-strand segment" is intended to refer to a segment of a nucleic acid segment that possesses a 3' and a 5' strand in which the base pairs are completely complementary for the length of the segment.

The term "single-strand segment" is intended to refer to a 3' or 5' segment of a nucleic acid segment that either (1) possesses a corresponding 3' and 5' strand in which the base pairs are not complementary or (2) lacks a corresponding 3' or a 5' strand.

The term "n region" is intended to refer to a region of a nucleic acid segment that possesses at least two contiguous guanine residues on the same strand (i.e., the 3' or the 5' strand) and which is located either at the ds/ss junction or a number of base pairs away from the ds/ss junction on the single strand. Preferably, the n region contains two additional guanine residues that correspond to the two contiguous guanine residues. However, the n region may also contain one additional guanine residue that corresponds to one of the contiguous guanine residues and either a thymine, uracil, or adenine residue that corresponds to the other contiguous guanine residue. Additionally, the n region could also contain one additional guanine residue that corresponds to one of the two contiguous guanine residues and lack a residue to correspond to the other contiguous guanine residue. Further, the n region could contain a thymine, uracil, or adenine residue that corresponds to one of the two contiguous guanine residues and lack a residue to correspond to the other contiguous guanine residue. Even further, the n region may further comprise two thymine, uracil, or adenine residues that corresponds to the two contiguous guanine residues. Finally, the two contiguous guanine residues of the n region may lack corresponding residues.

The term "complementary residue" is intended to refer to a nucleic acid residue that naturally pairs with the corresponding residue on the corresponding strand. The term "complements" is intended to define the relationship between the pairing of purines and pyrimidines in a nucleic acid segment. For example, one complementary pairing is the natural pairing of adenine with thymine or uracil. Another complementary pairing is the natural pairing of guanine with cytosine.

The term "non-complementary residue" is intended to refer to the situation in which a nucleic acid residue is "mismatched" in a base pair (i.e., a pyrimidine-pyrimidine pairing or a purine-purine pairing).

The term "purine" includes guanine and adenine.

The term "pyrimidine" includes thymine, uracil and cytosine.

The term "nucleic acid residue" is intended to broadly refer to the group consisting of guanine, cytosine, adenine, thymine, and uracil.

In the compound of formula I, the groups labeled $R_1$-$R_4$ can each be independently a 5 to 6 membered heterocycle containing 1-3 nitrogen atoms and optionally one oxygen atom, with the remainder of the atoms being carbon atoms. These heterocycles include, but are not limited to, pyrrolyl, 2-H pyrrolyl, 3H-pyrrolyl, pyrazolyl, 2H-imidazolyl, 1,2,3-triazolyl, 1,2,4-triazolyl, isoxozolyl, oxazolyl, 1,2,3-oxadiazolyl, 1,2,4-oxadiazolyl, 1,2,5-oxadiazolyl, 1,3,4-oxadiazolyl, 1,2,3,4-oxatriazolyl, 1,2,3,5-oxatriazolyl, pyridyl, pyridazyl, pyrimidinyl, pyrazyl, piperazyl, 1,3,5-triazyl, 1,2,4-triazyl, 1,2,3-triazyl, 4H-1,2-oxazyl, 2H-1,3-oxazyl, 6H-1,3-oxazyl, 6H-1,2-oxazyl, 1,4-oxazyl, 2H-1,2-oxazyl, 4H-1,4-oxazyl, 1,2,4-oxadiazyl, 1,3,5-oxadiazyl, pyrrolidinyl, piperidinyl, piperazinyl, pyrazinyl, 1,2,3,6-tetrahydropyridinyl, pyrazolinyl, pyrazolidinyl, pyridinyl, pyrazolyl, triazolyl, pyrazinyl, oxazolyl, pyridazinal, triazinyl, and morpholyl.

The 5 to 6 membered heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

Additionally, in the compound of formula I, the groups labeled $R_1$-$R_4$ can each be independently a 9-13 membered bicyclic heterocycle containing 1-3 nitrogen atoms and optionally one oxygen atom, with the remainder of the atoms being carbon atoms. These bicyclic heterocycles include, but are not limited to, indolyl, 3H-indolyl, cyclopenta[b]pyridinyl, pyrano[3,4-b]-pyrrolyl, indazolyl, benzisoxazolyl, benzoxazolyl, quinolinyl, isoquinolinyl, cinnolinyl, quinazolinyl, 1,8-naphthyridinyl, 1,7-naphthyridinyl, 1,6-naphthyridinyl, 2H-1,3-benzoxazine, 2H-1,4-benzoxazine, 1H-2,3-benzoxazine, 4H-3,1-benzoxazine, 2H-1,2-benzoxazine, and 4H-1,4-benzoxazine.

The 9-13 membered bicyclic heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

In formula I, groups $R_5$-$R_6$ are each independently an anion or uncharged species. Any physiologically acceptable or pharmaceutically acceptable anion can be used as a substituent for $R_5$-$R_6$. Said acceptable anions include, but are not limited to, any thiolate, nitrate, chloride, acetate, perchlorate, phosphate, bromide, fluoride, iodide, sulfate, trifluoromethanesulfonate, hexafluorophosphate, hexafluoroantimonate or any halide anion.

Additionally, in formula I, each $L_1$ is independently a $C_1$-$C_6$ alkyl or ether linkage, and $L_3$ is a direct bond. It is also preferred that the $L_1$ linkage is linked to a carbon atom of the heterocycle. It is also preferred that the $C_1$-$C_6$ alkyl linkage is an ethyl or methyl linkage.

All references to "halogen" include fluorine, chlorine, bromine, and iodine. All references to the alkyl groups include branched or unbranched alkyl groups. All references to "heteroaryl" are intended to include a monocyclic aromatic hydrocarbon group having 5 or 6 ring atoms, or a bicyclic aromatic group having 8 to 10 atoms, each containing 1-3 heteroatoms selected from O, S or N, with the remainder of the atoms being carbon. Examples of suitable heteroaryls include pyridinyl, pyrimidinyl, and pyrazinyl, pyridazinyl, pyrrolyl, furanyl, oxazolyl, isoxazolyl, thiazolyl, isobenzofuryl, benzofuryl, benzo[b]thiophenyl, benzo[c]thiophenyl, indolyl, 3H-indolyl, 1H-indolyl, cyclopenta[b]pyridinyl, pyrano[3,4-b]pyrrolyl, indazolyl, benzisoxazolyl, benzoxazolyl, 2,1-benzisoxazolyl, 2H-1-benzopyranyl, 2H-1-benzoyran-2-yl, 4H-1-benzopyran-4-yl, 1H-2-benzopyran-1-yl, 3H-2-benzopyran-1-yl, quinolinyl, isoquinolinyl, cinnolinyl, quinazolinyl, 1,8-naphthtyridinyl, 1,7-naphthtyridinyl, 1,5-naphthtyridinyl, 1,6-naphthtyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl, 4H-1,4-benzoxazinyl, and the like.

Further, $R_7$ is a halogen, hydrogen, hydroxy, or a $C_1$-$C_6$ alkyl group. $R_8$-$R_9$ are each independently a hydrogen, hydroxy, a $C_1$-$C_3$ alkyl group, or a halogen.

In the compound of formula II, groups $R_{21}$-$R_{24}$ can each independently be a 5 to 6 membered heterocycle containing 1-3 nitrogen atoms and optionally one oxygen atom, with the remainder of the atoms being carbon atoms. These heterocycles include, but are not limited to, pyrrolyl, 2-H pyrrolyl, 3H-pyrrolyl, pyrazolyl, 2H-imidazolyl, 1,2,3-triazolyl, 1,2,4-triazolyl, isoxozolyl, oxazolyl, 1,2,3-oxadiazolyl, 1,2,4-oxadiazolyl, 1,2,5-oxadiazolyl, 1,3,4-oxadiazolyl, 1,2,3,4-oxatriazolyl, 1,2,3,5-oxatriazolyl, pyridyl, pyridazyl, pyrimidinyl, pyrazyl, piperazyl, 1,3,5-triazyl, 1,2,4-triazyl, 1,2,3-triazyl, 4H-1,2-oxazyl, 2H-1,3-oxazyl, 6H-1,3-oxazyl, 6H-1,2-oxazyl, 1,4-oxazyl, 2H-1,2-oxazyl, 4H-1,4-oxazyl, 1,2,4-oxadiazyl, 1,3,5-oxadiazyl, pyrrolidinyl, piperidinyl, piperazinyl, pyrazinyl, 1,2,3,6-tetrahydropyridinyl, pyrazolinyl, pyrazolidinyl, pyridinyl, pyrazolyl, triazolyl, pyrazinyl, oxazolyl, pyridazinal, triazinyl, and morpholyl.

The 5 to 6 membered heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

Additionally, in the compound of formula II, the groups labeled $R_{21}$-$R_{24}$ can each be independently a 9-13 membered bicyclic heterocycle containing 1-3 nitrogen atoms and optionally one oxygen atom, with the remainder of the atoms being carbon atoms. These bicyclic heterocycles include, but are not limited to, indolyl, 3H-indolyl, cyclopenta[b]pyridinyl, pyrano[3,4-b]-pyrrolyl, indazolyl, benzisoxazolyl, benzoxazolyl, quinolinyl, isoquinolinyl, cinnolinyl, quinazolinyl, 1,8-naphthyridinyl, 1,7-naphthyridinyl, 1,6-naphthyridinyl, 2H-1,3-benzoxazine, 2H-1,4-benzoxazine, 1H-2,3-benzoxazine, 4H-3,1-benzoxazine, 2H-1,2-benzoxazine, and 4H-1,4-benzoxazine.

The 9-13 membered bicyclic heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

All references to "halogen" include fluorine, chlorine, bromine, and iodine. All references to the alkyl groups include branched or unbranched alkyl groups. All references to "heteroaryl" are intended to include a monocyclic aromatic hydrocarbon group having 5 or 6 ring atoms, or a bicyclic aromatic group having 8 to 10 atoms, each containing 1-3 heteroatoms selected from O, S or N, with the remainder of the atoms being carbon. Examples of suitable heteroaryls include pyridinyl, pyrimidinyl, and pyrazinyl, pyridazinyl, pyrrolyl, furanyl, oxazolyl, isoxazolyl, thiazolyl, isobenzofuryl, benzofuryl, benzo[b]thiophenyl, benzo[c]thiophenyl, indolyl, 3H-indolyl, 1H-indolyl, cyclopenta[b]pyridinyl, pyrano[3,4-b]pyrrolyl, indazolyl, benzisoxazolyl, benzoxazolyl, 2,1-benzisoxazolyl, 2H-1-benzopyranyl, 2H-1-benzoyran-2-yl, 4H-1-benzopyran-4-yl, 1H-2-benzopyran-1-yl, 3H-2-benzopyran-1-yl, quinolinyl, isoquinolinyl, cinnolinyl, quinazolinyl, 1,8-naphthtyridinyl, 1,7-naphthtyridinyl, 1,5-naphthtyridinyl, 1,6-naphthtyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl, 4H-1,4-benzoxazinyl, and the like.

Additionally, in formula II, each $L_{21}$ linkage is independently a $C_1$-$C_6$ alkyl or ether linkage. Preferably, the $L_{21}$ linkage is linked to a carbon atom of the heterocycle. It is also preferred that the $C_1$-$C_6$ alkyl linkage is a methyl or ethyl linkage. Further, $R_{25}$ is a halogen, hydrogen, hydroxy, or a $C_1$-$C_6$ alkyl group. $R_{26}$-$R_{27}$ are each independently a hydrogen, hydroxy, a $C_1$-$C_3$ alkyl group, or a halogen.

The compounds of formulas I and II have been found to be effective in treating cancer. Some types of cancer that the compounds of formulas I and II have been found to be effective in treating are leukemia, non-small cell lung cancer, colon cancer, central nervous system cancer, melanoma, ovarian cancer, renal cancer, ovarian cancer, cancer of the head and neck, bladder cancer, small cell cancer of the lung, squamous-cell carcinomas of the head, neck, esophagus, skin, and the genitourinary tract, including the cervix, vulva, scrotum, and penis, prostate cancer, and breast cancer. The compounds of formulas I and II are, therefore, suitable for use in methods for treating cancer, cancer cells, or tumors, whether the compound of formula I or II is used alone or in conjunction with another compound of formula I or formula II or another known anti-cancer agent.

Such methods comprise administering to a patient in need of such treatment an anti-cancer, anti-tumor, or anti-cancer cell effective amount (hereinafter "effective amount") of one or more compounds of formulas I and/or II. The effective amount of the compound(s) of formulas I and/or II are preferably administered in any conventional form suitable for oral administration, for example in the form of a tablet, caplet, capsule, beadlet or powder. Additionally, dosage forms include troches, dispersions, suspensions, solutions, injections, infusions, creams, ointments, aerosols, and the like. These administration forms may be presented in unit dosage form and may be prepared by any of the methods well-known in the art of pharmacy. The compound(s) of formula I and/or II is/are present in an amount of from 1 to 99% by weight, based upon the total weight of the dosage form, for example from 10 to 50% by weight.

Additionally, the compound(s) of formula I and/or II can be administered in any other form suitable for rectal, topical, parenteral, intraperitoneal, ocular, pulmonary, inhalation, intramuscular, intravenous, and vaginal administration. The compound(s) of formula I and/or formula II is/are present in the dosage form in an amount of from 1 to 99% by weight, based upon the total weight of the dosage form, for example from 10 to 50% by weight.

The magnitude of a dose administered, however, varies according to the age, weight, sex, and response of the individual patient. In general, the daily dose range of a compound of formula I or II (or of any mixture thereof) is within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases. These dosages may fall within the range of 0.00001 to 500 mg administered to the patient per day. When the composition is in the form of an oral composition, the weight of the compound(s) of formula I and/or formula II in the composition may be in the range of from 0.00001 to 500 mg, such as from 5 to 250 mg or from 10 to 200 mg. If the compound(s) of formula I and/or formula II is/are in the form of a tablet, the tablet may be uncoated or coated and the coating may be a conventional coating and the coating may be applied by a conventional method.

A pharmaceutical composition with a compound (or compounds) of formula I and/or formula II as an active ingredient (or a pharmaceutically acceptable salt thereof), may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. Said pharmaceutical composition contains a pharmaceutically effective amount of at least one compound of formula I and/or formula II. Further, the pharmaceutical composition is pharmaceutically effective against cancer, including leukemia, non-small cell lung cancer, colon cancer, central nervous system cancer, melanoma, ovarian cancer, renal cancer, ovarian cancer, cancer of the head and neck, bladder cancer, small cell cancer of the lung, squamous-cell carcinomas of the head, neck, esophagus, skin, and the genitourinary tract, including the cervix, vulva, scrotum, and penis, prostate cancer, and breast cancer.

The dosage may be administered in either one single dosage, two dosages, or in more than two dosages per day.

The compounds of formula I and formula II have been found to exhibit a remarkable ability to oxidize guanines and thereby promote specific strand scission at the n region of nucleic acid segments having a hairpin or frayed duplex structure. Scission occurs upon exposure to piperidine. Preferably, the piperidine used is in the range of 50 mM to 5,000 mM, and more preferably 200 mM.

Oxidation and scission minimally requires at least two guanine residues in the n region of the nucleic acid segment. Selective strand scission is preferably conducted in the presence of dioxygen.

The time required to oxidize at least one of the guanine residues of the n region is normally between 0 (instant) and 60 minutes. This time will be increased (usually) if the oxidation of more than one of the guanine residues of the n position is desired.

The time required to split (if the nucleic acid segment is exposed to piperidine) the nucleic acid segment is normally between 0 (instant) and 120 minutes, preferably 30 minutes. However, the time required to split the nucleic acid segment may be adjusted according to the composition of the nucleic acid segments and the presence and amount of dioxygen. Additionally, the reaction to split the nucleic acid segment may be carried out in the temperature range of 45-100° C., preferably 90° C.

The nucleic acid segment is preferably longer than 5 nucleotides in length, for example between 5 and 1,000,000 nucleotides in length, more preferably between 5 and 100,000 nucleotides in length, even more preferably between 5 and 50,000 nucleotides in length, even further preferred is a segment that is between 5 and 10,000 nucleotides in length, and most preferred is a segment that is between 5 and 1,000 nucleotides in length. Also preferred are segments of between 10, 20, or 30 and 1,000 nucleotides in length.

Additionally, the n region of the nucleic acid segment may be located a number of base pairs away from the ds/ss junction on the single-strand. Preferably, the number of base pairs is between 1 and 1,000,000. Even more preferably, it is between 1 and 100,000. Further preferred is a range of 1 and 10,000. More further preferred is a range of 1 and 1,000. Even more further preferred is a range of 1 to 100. More preferred still is a range of 1 to 50. Even more preferred still is a range of 1 to 10 base pairs. More preferred even still is a range of 1-5 base pairs. The most preferred range is a range of 1-2 base pairs.

Finally, it is noted that when the n region is located at least 5 base pairs away from the ds/ss junction on the single strand and not on the ds/ss junction, one or both of the two contiguous guanine residues can correspond to cytosine residues.

The following are incorporated by reference in their entirety:

1) "Recognition and Strand Scission at Junctions between Single- and Double-stranded DNA by a Trinuclear Copper Complex" by Kristi J. Humphreys, Kenneth D. Karlin, and Steven E. Rokita, J. Am. Chem Soc. 2001, 123, 5588-5589.
2) The Handbook of Chemistry and Physics (82nd Edition) edited by David R. Lide.
3) "A new trinuclear complex and its reactions with plasmid DNA" by Steven T. Frey, Helen H. J. Sun, Narasimha N. Murthy, and Kenneth D. Karlin, Inorganica Chimica Acta 242 (1996) 329-338.
4) "Targeted Strand Scission of DNA Substrates by a Tricopper II Coordination Complex" by Kristi J. Humphreys, Kenneth D. Karlin, and Steven E. Rokita, J. Am. Chem Soc. 2002, 124, p. 8055-8066
5) "Goodman and Gilman's The Pharmaceutical Basis of Therapeutics" edited by Alfred Goodman Gilman, Theodore W. Rall, Alan S. Nies, and Palmer Taylor (8th Edition).
6) "Goodman and Gilman's The Pharmaceutical Basis of Therapeutics" edited by Joel G. Hardman, Lee E. Limbard, Perry B. Molinoff, Raymond W. Ruddon (9th Edition).
7) "Goodman and Gilman's The Pharmaceutical Basis of Therapeutics" edited by Joel G. Hardman, Lee E. Limbard, and Alfred Goodman Gilman (10th Edition).
8) U.S. Provisional Application No. 60/331,197.
9) U.S. Provisional Application No. 60/331,198.
10) "Oxidative strand scission of nucleic acids by a multinuclear copper (II) complex" by Kristi J. Humphreys, Anne E. Johnson, Kenneth D. Karlin, and Steven E. Rokita, J. Biol. Inorg. Chem. (2002) 7: 835-842.
11) "Efficient and Specific Strand Scission of DNA by a Dinuclear Copper Complex: Comparative Reactivity of Complexes with Linked ris(2-pyridylmethyl)amine Moieties" by Kristi J. Humphreys, Kenneth D. Karlin, and Steven E. Rokita, J. Am. Chem. Soc. (2002) 124: 6009-6019.

EXAMPLES

Example 1

The compound of formula I having the following structure (hereinafter the binuclear complex), wherein PY is 2-pyridil:

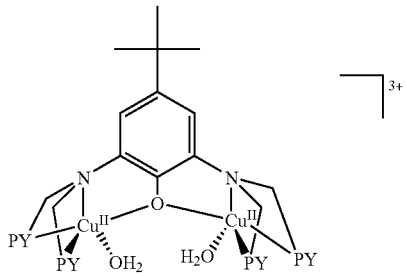

was prepared by taking 200 mg (0.58 mmol) of $Cu(ClO_4)_2 \cdot 6H_2O$ dissolved in 3 mL of $H_2O$ and introducing 160.0 mg (0.29 mmol) of a ligand of formula II having the following structure, wherein PY is 2-pyridil:

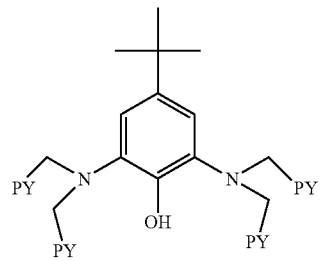

in warm EtOH (3 mL). A dark green solution was immediately formed and evaporation of the solvent under a flow of argon overnight results in the production of bright greenish-blue crystals. These crystals were then filtered in air and washed with $H_2O$ and then with EtOH to yield 0.28 g of the binuclear complex.

Example 2

Copper-dependent strand scission was tested by combining various concentrations of the binuclear copper complex (1 μM-1 mM, preferably 100 μM) with a labeled DNA sample (1 pM-100 mM, preferably 100 nm, and 1-1000 nCi, preferably 90 nCi) in a sodium phosphate buffer (10 mM, pH 7.5) and strand scission was initiated by the addition of a reductant (5 mM), which is preferably a thiol, and more preferably mercaptopropionic acid (MPA). Preferably the reductant is 1 μM-100 mM and preferably 5 mM. The reaction was quenched after a 15 minute incubation at ambient temperature with the addition of 10 mM of diethyl dithiocarbanic acid (5 μL). The DNA was then isolated by ethanol precipitation and then dried under high vacuum. Additionally, when scission was desired, some samples were further treated with 20 μL piperidine (0.2 M) for 30 minutes at 90° C. These samples were dried under reduced pressure and twice redissolved with 20 μL water, and then subsequently dried to remove any trace amounts of piperidine. The isolated DNA was then suspended in water, normalized to 45 nCi per sample, mixed with a loading buffer (0.25% bromphenol blue, 0.25% xylene cyanole, 3% sucrose, and 7 M urea). The samples with loading buffer were then separated by denaturing (7 M urea) polyacrylamide (20%) gel electrophoresis and visualized by autoradiography and Phosphorimager (Molecular Dynamics). Quantitation of the products relied upon ImageQuant software.

Specific strand scission was observed at the oxidized guanine.

Example 3

Referring to FIG. 2a, it was determined that the binuclear complex would oxidize (and cleave if exposed to piperidine) the nucleic acid segment at one of the guanine residues in the n region 12% and 9% of the time (said percentages being (a) reported in clockwise fashion and (b) relative to the percent reactivity of that position when the 5' end of that strand contains a radioactive label).

Referring to FIG. 2b, it was determined that the binuclear complex would oxidize (and cleave if exposed to piperidine) the nucleic acid segment at one of the guanine residues in the n region 7% and 9% of the time said percentages being (a) reported in clockwise fashion and (b) relative to the percent reactivity of that position when the 5' end of that strand contains a radioactive label).

Referring to FIG. 2c, it was determined that the binuclear complex would oxidize (and cleave if exposed to piperidine) the nucleic acid segment at one of the guanine residues in the n region 19%, 13%, and 8% of the time said percentages being (a) reported in clockwise fashion and (b) relative to the percent reactivity of that position when the 5' end of that strand contains a radioactive label).

Referring to FIG. 2d, it was determined that the binuclear complex would oxidize (and cleave if exposed to piperidine) the nucleic acid segment at one of the guanine residues in the n region 15%, 17%, and 26% of the time said percentages being (a) reported in clockwise fashion and (b) relative to the percent reactivity of that position when the 5' end of that strand contains a radioactive label).

Referring to FIG. 2e, it was determined that the binuclear complex would oxidize (and cleave if exposed to piperidine) the nucleic acid segment at one of the guanine residues in the n region 31%, 20%, 33%, and 36% of the time said percentages being (a) reported in clockwise fashion and (b) relative to the percent reactivity of that position when the 5' end of that strand contains a radioactive label).

Example 4

Figure 3:
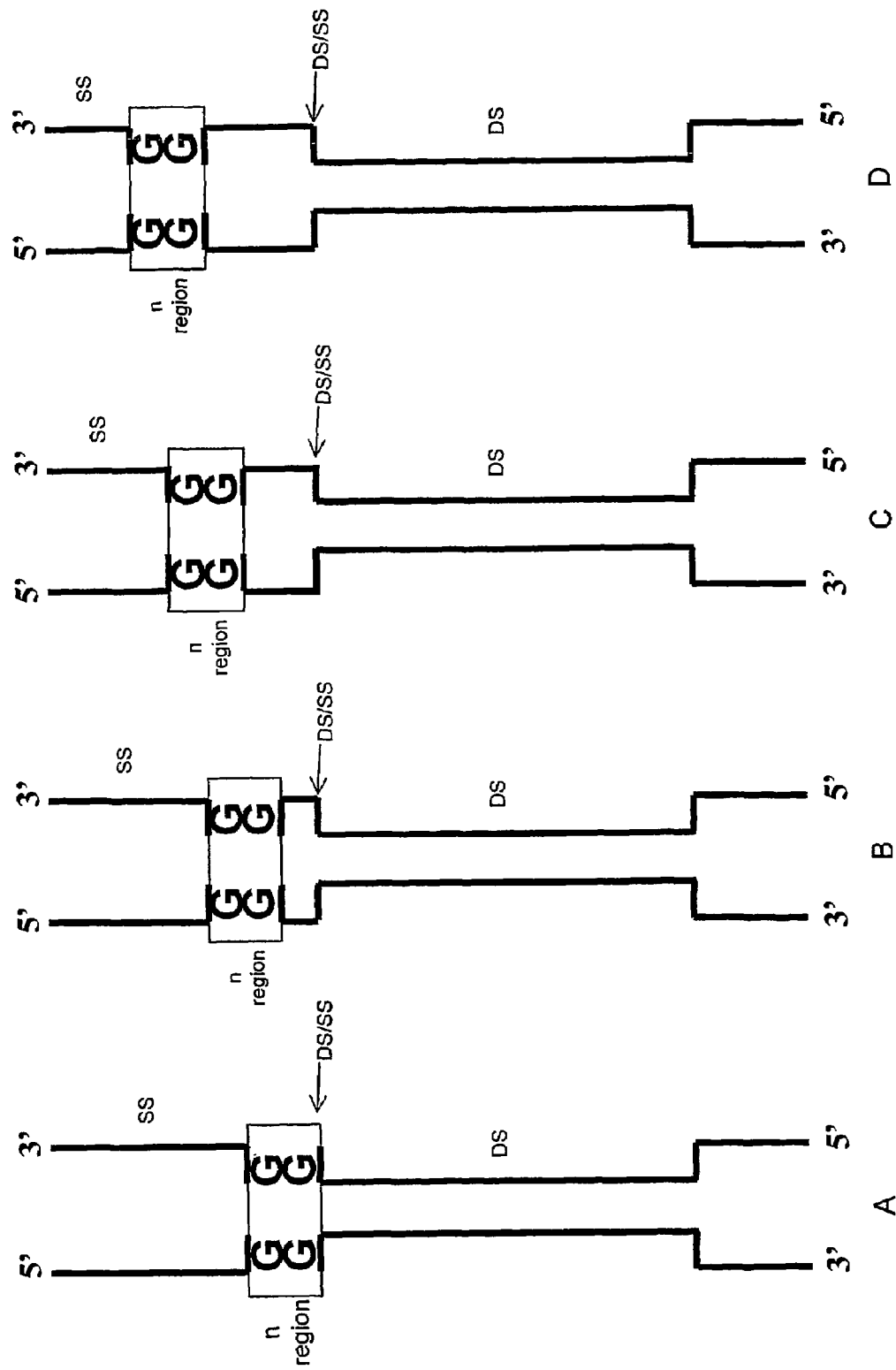

Referring to FIG. 3a, it was determined that the binuclear complex would oxidize (and cleave if exposed to piperine) the nucleic acid segment at one of the guanine residues in the n region 37%, 26%, 38%, and 46% of the time (said percentages being (a) reported in clockwise fashion (starting from the guanine residue on the top right) and (b) relative to the percent reactivity of that position when the 5' end of that strand contains a radioactive label).

Referring to FIG. 3b, it was determined that the binuclear complex would oxidize (and cleave if exposed to piperine) the nucleic acid segment at one of the guanine residues in the n region 24%, 20%, 31%, and 39% of the time (said percentages being (a) reported in clockwise fashion (starting from the guanine residue on the top right) and (b) relative to the percent reactivity of that position when the 5' end of that strand contains a radioactive label).

Referring to FIG. 3c, it was determined that the binuclear complex would oxidize (and cleave if exposed to piperine) the nucleic acid segment at one of the guanine residues in the n region 7%, 22%, 23%, and 14% of the time (said percentages being (a) reported in clockwise fashion (starting from the guanine residue on the top right) and (b) relative to the percent reactivity of that position when the 5' end of that strand contains a radioactive label).

Referring to FIG. 3d, it was determined that the binuclear complex would oxidize (and cleave if exposed to piperine) the nucleic acid segment at one of the guanine residues in the n region 8%, 13%, 29%, and 23% of the time (said percentages being (a) reported in clockwise fashion (starting from the guanine residue on the top right) and (b) relative to the percent reactivity of that position when the 5' end of that strand contains a radioactive label).

Therefore, FIGS. 3a-3d show that maximum reactivity between the binuclear complex and the n region will occur when the n region is located at the ds/ss junction. However, reactions between the binuclear complex and the n region will still occur (although with decreased frequency) even as the n region is moved away from the ds/ss junction on the single-strand segment of the nucleic acid segment.

We claim:

1. A method of treating a cancer selected from the group consisting of leukemia, non-small cell lung cancer, colon cancer, central nervous system cancer, melanoma, ovarian cancer, renal cancer, ovarian cancer, prostate cancer, and breast cancer, in a patient in need thereof, said method comprising administering to a patient a cancer-treating effective amount of a compound of formula I

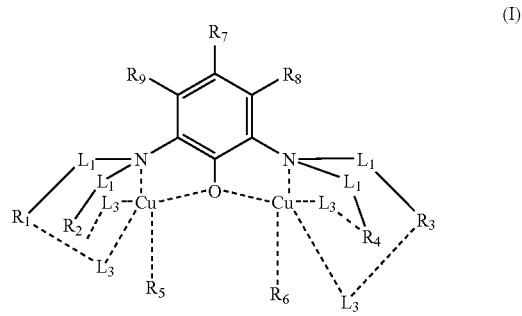

(I)

wherein $R_1$-$R_4$ are each independently pyridyl, wherein the pyridyl is linked to a respective linkage $L_3$ through a nitrogen atom of the pyridyl, and wherein the pyridyl is linked to a respective linkage $L_1$ through any of the nitrogen or carbon atoms of the pyridyl other than the nitrogen atom that links to linkage $L_3$;

$R_5$-$R_6$ are each independently an anion or uncharged species;

$R_7$ is a hydrogen, halogen, hydroxy, or a $C_1$-$C_6$ alkyl group;

$R_8$-$R_9$ are each independently a hydrogen, hydroxy, a $C_1$-$C_3$ alkyl group, or a halogen;

each $L_1$ is independently a $C_1$-$C_6$ alkyl or ether linkage; and each $L_3$ is a direct bond.

2. A method of treating cancer cells, wherein the cancer cells selected from the group consisting of leukemia cells, non-small cell lung cancer cells, colon cancer cells, central nervous system cancer cells, melanoma cells, ovarian cancer cells, renal cancer cells, ovarian cancer cells, prostate cancer cells, and breast cancer cells, said method comprising administering to the cancer cells a cancer cell-treating effective amount of a compound of formula I

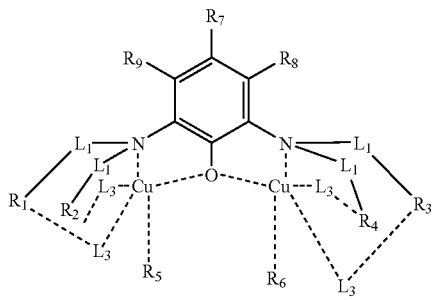

(I)

wherein
- $R_1$-$R_4$ are each independently pyridyl, wherein the pyridyl is linked to a respective linkage $L_3$ through a nitrogen atom of the pyridyl, and wherein the pyridyl is linked to a respective linkage $L_1$ through any of the nitrogen or carbon atoms of the pyridyl other than the nitrogen atom that links to linkage $L_3$;
- $R_5$-$R_6$ are each independently an anion or uncharged species;
- $R_7$ is a hydrogen, halogen, hydroxy, or a $C_1$-$C_6$ alkyl group;
- $R_8$-$R_9$ are each independently a hydrogen, hydroxy, a $C_1$-$C_3$ alkyl group, or a halogen;
- each $L_1$ is independently a $C_1$-$C_6$ alkyl or ether linkage; and
- each $L_3$ is a direct bond.

3. A method of oxidizing a nucleic acid segment at a specific position thereon, wherein said method comprises
    (A) providing a nucleic acid segment having at least one double-strand segment and at least one single-strand segment, and including an n region, wherein said n region is located either at or a number of base pairs from a double-strand/single-strand (ds/ss) junction on the single-strand segment of the nucleic acid segment, and the n region comprises two contiguous guanine residues located on a same strand of the nucleic acid segment; and
    (B) contacting the nucleic acid segment with a compound of formula I for a time sufficient to oxidize at least one of the guanine residues of the n region

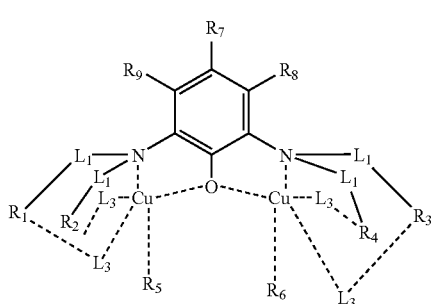

(I)

wherein
- $R_1$-$R_4$ are each independently pyridyl, wherein the pyridyl is linked to a respective linkage $L_3$ through a nitrogen atom of the pyridyl, and wherein the pyridyl is linked to a respective linkage $L_1$ through any of the nitrogen or carbon atoms of the pyridyl other than the nitrogen atom that links to linkage $L_3$;
- $R_5$-$R_6$ are each independently an anion or uncharged species;

$R_7$ is a hydrogen, halogen, hydroxy, or a $C_1$-$C_6$ alkyl group;
$R_8$-$R_9$ are each independently a hydrogen, hydroxy, a $C_1$-$C_3$ alkyl group, or a halogen;
each $L_1$ is independently a $C_1$-$C_6$ alkyl or ether linkage; and
each $L_3$ is a direct bond.

4. A method of treating a cancer selected from the group consisting of leukemia, non-small cell lung cancer, colon cancer, central nervous system cancer, melanoma, ovarian cancer, renal cancer, ovarian cancer, prostate cancer, and breast cancer, in a patient in need thereof, said method comprising administering to a patient a cancer-treating effective amount of a compound of formula II

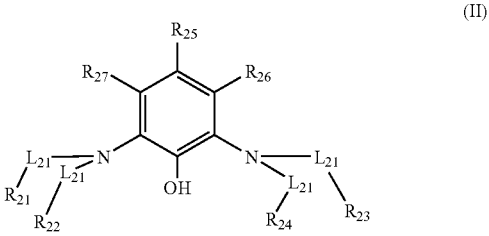

(II)

wherein
- $R_{21}$-$R_{24}$ are each independently pyridyl, wherein the pyridyl is linked to a respective linker $L_{21}$ through a carbon or nitrogen atom of the pyridyl;
- $R_{25}$ is a hydrogen, halogen, hydroxy, or a $C_1$-$C_6$ alkyl group;
- $R_{26}$-$R_{27}$ are each independently a hydrogen, hydroxy, a $C_1$-$C_3$ alkyl group, or a halogen; and
- each $L_{21}$ is independently a $C_1$-$C_6$ alkyl or ether linkage.

5. A method of treating cancer cells, wherein the cancer cells selected from the group consisting of leukemia cells, non-small cell lung cancer cells, colon cancer cells, central nervous system cancer cells, melanoma cells, ovarian cancer cells, renal cancer cells, ovarian cancer cells, prostate cancer cells, and breast cancer cells, said method comprising administering to the cancer cells a cancer cell-treating effective amount of a compound of formula II

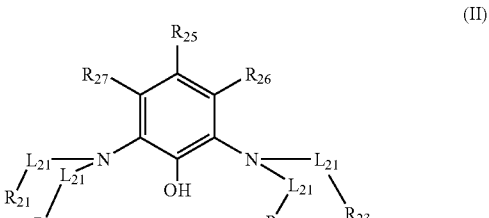

(II)

wherein
- $R_{21}$-$R_{24}$ are each independently pyridyl, wherein the pyridyl is linked to a respective linker $L_{21}$ through a carbon or nitrogen atom of the pyridyl;
- $R_{25}$ is a hydrogen, halogen, hydroxy, or a $C_1$-$C_6$ alkyl group;
- $R_{26}$-$R_{27}$ are each independently a hydrogen, hydroxy, a $C_1$-$C_3$ alkyl group, or a halogen; and
- each $L_{21}$ is independently a $C_1$-$C_6$ alkyl or ether linkage.

6. A pharmaceutical composition comprising at least one compound of formula I

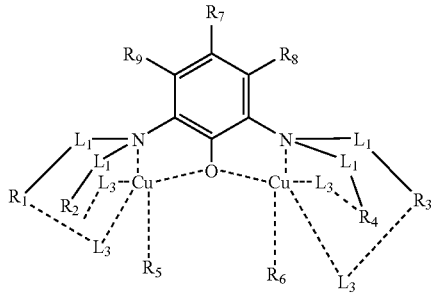

(I)

wherein $R_1$-$R_4$ are each independently, wherein the pyridyl is linked to a respective linkage $L_3$ through a nitrogen atom of the pyridyl, and wherein the pyridyl is linked to a respective linkage $L_1$ through any of the nitrogen or carbon atoms of the pyridyl other than the nitrogen atom that links to linkage $L_3$;

$R_5R_6$ are each independently an anion or uncharged species;

$R_7$ is a hydrogen, halogen, hydroxy, or a $C_1$-$C_6$ alkyl group;

$R_8$-$R_9$ are each independently a hydrogen, hydroxy, a $C_1$-$C_3$ alkyl group, or a halogen;

each $L_1$ is independently a $C_1$-$C_6$ alkyl or ether linkage; and each $L_3$ is a direct bond, and one or more pharmaceutically acceptable excipients.

7. A pharmaceutical composition comprising at least one compound of formula II

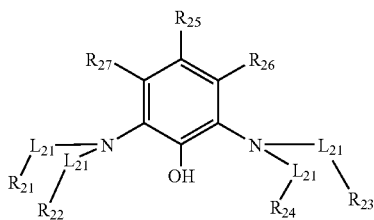

(II)

wherein $R_{21}$-$R_{24}$ are each independently, wherein the pyridyl is linked to a respective linker $L_{21}$ through a carbon or nitrogen atom of the pyridyl;

$R_{25}$ is a hydrogen, halogen, hydroxy, or a $C_1$-$C_6$ alkyl group;

$R_{26}$-$R_{27}$ are each independently a hydrogen, hydroxy, a $C_1$-$C_3$ alkyl group, or a halogen; and each $L_{21}$ is independently a $C_1$-$C_6$ alkyl or ether linkage; and one or more pharmaceutically acceptable excipients.

8. A method of splitting a nucleic acid segment at a specific position thereon, wherein said method comprises (A) providing a nucleic acid segment having at least one double-strand segment and at least one single-strand segment, and including an n region, wherein said n region is located either at or a number of base pairs from a double-strand/single-strand (ds/ss) junction on the single-strand segment of the nucleic acid, and the n region comprises two contiguous guanine residues located on a same strand of the nucleic acid segment;

(B) contacting the nucleic acid segment with a compound of formula I for a time sufficient to oxidize at least one of the guanine residues of the n region; and (C) thereafter contacting the nucleic acid segment with an amount of piperidine for a time sufficient to split the nucleic acid segment at the at least one oxidized guanine

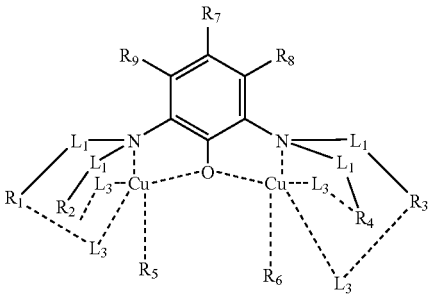

(I)

wherein $R_1$-$R_4$ are each independently pyridyl, wherein the pyridyl is linked to a respective linkage $L_3$ through a nitrogen atom of the pyridyl, and wherein the pyridyl is linked to a respective linkage $L_1$ through any of the nitrogen or carbon atoms of the pyridyl other than the nitrogen atom that links to linkage $L_3$;

$R_5R_6$ are each independently an anion or uncharged species;

$R_7$ is a hydrogen, halogen, hydroxy, or a $C_1$-$C_6$ alkyl group;

$R_6$-$R_9$ are each independently a hydrogen, hydroxy, a $C_1$-$C_3$ alkyl group, or a halogen;

each $L_1$ is independently a $C_1$-$C_6$ alkyl or ether linkage; and each $L_3$ is a direct bond.

9. The method of claim 8, wherein the n region further comprises one additional guanine residue that corresponds to one of the two contiguous guanine residues.

10. The method of claim 8, wherein the n region further comprises two additional guanine residues, wherein said two additional guanine residues correspond to the two contiguous guanine residues.

11. The method of claim 8, wherein the number of base pairs is between one and 1,000.

12. The method of claim 11, wherein the number of base pairs is between one and 100.

13. The method of claim 12, wherein the number of base pairs is between one and 10.

14. The method of claim 3, wherein the n region further comprises one additional guanine residue that corresponds to one of the two contiguous guanine residues.

15. The method of claim 3, wherein the n region further comprises two additional guanine residues, wherein said two additional guanine residues correspond to the two contiguous guanine residues.

16. The method of claim 3, wherein the number of base pairs is between one and 1,000.

17. The method of claim 16, wherein the number of base pairs is between one and 100.

18. The method of claim 17, wherein the number of base pairs is between one and 10.

19. The method of claim 1, wherein the compound of formula (I) is:

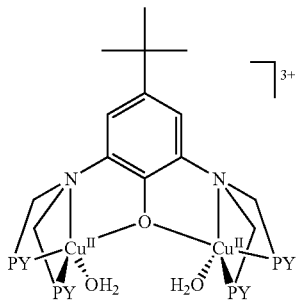

and wherein PY is 2-pyridyl.

20. The method of claim 2, wherein the compound of formula (I) is:

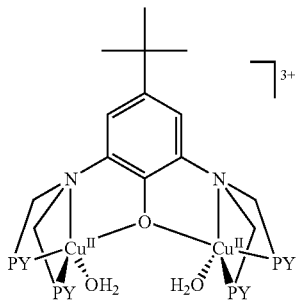

and wherein PY is 2-pyridyl.

21. The method of claim 3, wherein the compound of formula (I) is:

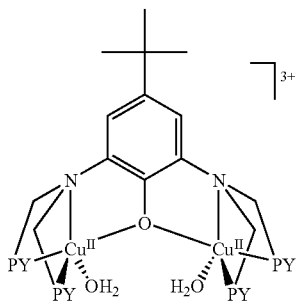

and wherein PY is 2-pyridyl.

22. The method of claim 4, wherein the compound of formula (II) is:

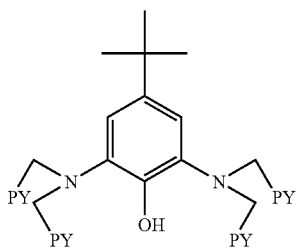

and wherein PY is 2-pyridyl.

23. The method of claim 5, wherein the compound of formula (II) is:

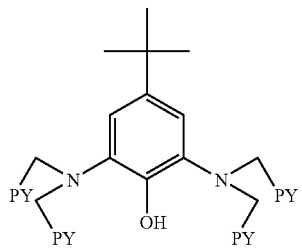

and wherein PY is 2-pyridyl.

24. The composition of claim 6, wherein the compound of formula (I) is:

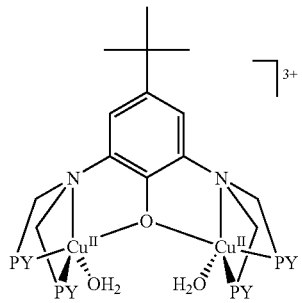

and wherein PY is 2-pyridyl.

25. The composition of claim 7, wherein the compound of formula (II) is:

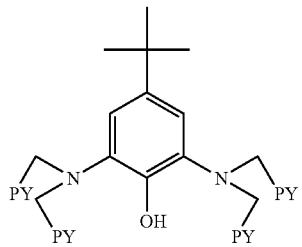

and wherein PY is 2-pyridyl.

26. The method of claim 8, wherein the compound of formula (I) is:

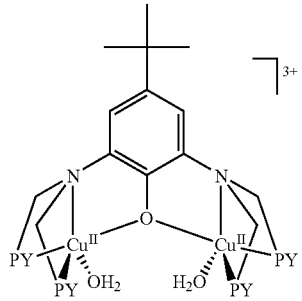

and wherein PY is 2-pyridyl.

* * * * *